US00PP18307P2

(12) United States Plant Patent
Meszaros

(10) Patent No.: US PP18,307 P2
(45) Date of Patent: Dec. 11, 2007

(54) ***IPOMOEA* PLANT NAMED 'EMERALD SPLASH'**

(50) Latin Name: *Ipomoea batatas*
Varietal Denomination: Emerald Splash

(75) Inventor: Debra Meszaros, Riverhead, NY (US)

(73) Assignee: Advanced Plant Technologies LLC, Riverhead, NY (US)

( * ) Notice: Subject to any disclaimer, the term of this patent is extended or adjusted under 35 U.S.C. 154(b) by 0 days.

(21) Appl. No.: 11/438,531

(22) Filed: May 22, 2006

(51) Int. Cl.
*A01H 5/00* (2006.01)

(52) U.S. Cl. ..... Plt./258

(58) Field of Classification Search ..... None
See application file for complete search history.

*Primary Examiner*—Wendy C. Haas
(74) *Attorney, Agent, or Firm*—C. A. Whealy

(57) ABSTRACT

A new and distinct cultivar of *Ipomoea* plant named 'Emerald Splash', characterized by its compact, mounding and outwardly spreading growth habit; freely branching plant habit; light yellow-green and green variegated foliage.

2 Drawing Sheets

Botanical designation: *Ipomoea batatas.*
Cultivar denomination: 'Emerald Splash'.

BACKGROUND OF THE INVENTION

The present invention relates to a new and distinct cultivar of *Ipomoea,* botanically known as *Ipomoea batatas,* and hereinafter referred to by the name 'Emerald Splash'.

The new *Ipomoea* is a product of a planned breeding program conducted by the Inventor in Riverhead, N.Y. The objective of the breeding program is to create new compact *Ipomoea* cultivars with attractive foliage shape and coloration.

The new *Ipomoea* is a naturally-occurring whole plant mutation of the *Ipomoea batatas* cultivar Ivory Jewel, not patented. The new *Ipomoea* was discovered and selected by the Inventor from within a population of plants of 'Ivory Jewel' in a controlled environment in Riverhead, N.Y. on May 4, 2004.

Asexual reproduction of the new *Ipomoea* by terminal cuttings in a controlled environment in Riverhead, N.Y. since February, 2005, has shown that the unique features of this new *Ipomoea* are stable and reproduced true to type in successive generations.

SUMMARY OF THE INVENTION

The cultivar Emerald Splash has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Emerald Splash'. These characteristics in combination distinguish 'Emerald Splash' as a new and distinct cultivar of *Ipomoea:*

1. Compact, mounding and outwardly spreading growth habit.
2. Freely branching plant habit.
3. Light yellow-green and green variegated foliage.

Plants of the new *Ipomoea* can be compared to plants of the parent, the cultivar Ivory Jewel. Plants of the new

*Ipomoea* differ from plants of the cultivar Ivory Jewel in the following characteristics:

1. Plants of the new *Ipomoea* are much more compact and less vigorous than plants of the cultivar Ivory Jewel.
2. Plants of the new *Ipomoea* are more freely branching and have shorter internodes than plants of the cultivar Ivory Jewel.
3. Plants of the new *Ipomoea* have smaller leaves than plants of the cultivar Ivory Jewel.
4. Plants of the new *Ipomoea* have light yellow green and green variegated foliage whereas plants of the cultivar Ivory Jewel have less striking yellow green and dark green variegated foliage.

Plants of the new *Ipomoea* can be compared to plants of the *Ipomoea batatas* cultivar Ace of Spades, not patented. In side-by-side comparisons conducted in Riverhead, N.Y., plants of the new *Ipomoea* differed from plants of the cultivar Ace of Spades in the following characteristics:

1. Plants of the new *Ipomoea* were more compact and less vigorous than plants of the cultivar Ace of Spades.
2. Plants of the new *Ipomoea* and the cultivar Ace of Spades differed in leaf color as plants of the cultivar Ace of Spades had maroon-colored leaves.

BRIEF DESCRIPTION OF THE PHOTOGRAPHS

The accompanying colored photographs illustrate the overall appearance of the new *Ipomoea,* showing the colors as true as it is reasonably possible to obtain in colored reproductions of this type. Colors in the photographs may differ slightly from the color values cited in the detailed botanical description which accurately describe the colors of the new *Ipomoea.*

The photograph on the first sheet comprises a side perspective view of a typical plant of 'Emerald Splash' grown in a container.

The photograph on the second sheet comprises a side perspective comparison view of typical plants of 'Emerald Splash' (left) and 'Ivory Jewel' (right).

DETAILED BOTANICAL DESCRIPTION

The photographs and following observations, measurements and values describe plants grown in Riverhead, N.Y. in a polyethylene-covered greenhouse during the spring and summer under conditions which closely approximate commercial production. During the production of the plants, day temperatures were about 22° C., night temperatures were about 17° C. and light levels ranged from 3,000 to 8,000 foot-candle. Plants were about 14 weeks old when the photographs and the description were taken. In the detailed description, color references are made to The Royal Horticultural Society Colour Chart, 2001 Edition, except where general terms of ordinary dictionary significance are used.

Botanical classification: *Ipomoea batatas* cultivar Emerald Splash.

Parentage: Naturally-occurring whole plant mutation of the *Ipomoea batatas* cultivar Ivory Jewel, not patented.

Propagation:

*Type.*—By terminal cuttings.

*Time to initiate roots, summer.*—About five days at temperatures of 22° C.

*Time to initiate roots, winter.*—About seven days at temperatures of 22° C.

*Time to produce a rooted young plant, summer.*—About 21 days at temperatures of 22° C.

*Time to produce a rooted young plant, winter.*—About 23 days at temperatures of 22° C.

*Root description.*—Fine to thick; white in color.

*Rooting habit.*—Freely branching; dense.

Plant description:

*Plant habit.*—Compact; mounding and outwardly spreading. Freely branching; about three to five lateral branches per plant; pinching enhances lateral branch development.

*Plant height.*—About 11 cm.

*Plant diameter.*—About 25 cm.

Lateral branch description:

*Length.*—About 20 cm to 25 cm.

*Diameter.*—About 3 mm.

*Internode length.*—About 3 mm to 5 mm.

*Strength.*—Strong.

*Texture.*—Smooth, glabrous.

*Color.*—N144D.

Foliage description:

*Arrangement.*—Opposite, simple.

*Length.*—About 6 cm to 8 cm.

*Width.*—About 4 cm to 6 cm.

*Shape.*—Roughly cordate.

*Apex.*—Acute.

*Base.*—Obtuse to cordate.

*Margin.*—Entire.

*Texture, upper and lower surfaces.*—Smooth, glabrous.

*Venation pattern.*—Pinnate.

*Color.*—Developing foliage, upper surface: Random sectors of 4A, 4D, N144B and 143B. Developing foliage, lower surface: Random sectors of 4D and 143B. Fully developed foliage, upper surface: Random sectors of 150D and 139B; at the margin, 63A; venation, 150D. Fully developed foliage, lower surface: Random sectors of 150D and 143A; venation, 150D.

*Petiole.*—Length: About 5 cm to 7 cm. Diameter: About 3 mm. Texture, upper and lower surfaces: Smooth, glabrous. Color, upper and lower surfaces: 144C.

Flower description: Flower initiation and development has not been observed on plants of the new *Ipomoea.*

Temperature tolerance: Plants of the new *Ipomoea* have been observed to tolerate temperatures from about 10° C. to about 32° C.

Pathogen/pest resistance: Plants of the new *Ipomoea* have not been observed to be resistant to pests and pathogens common to *Ipomoea.*

It is claimed:

1. A new and distinct *Ipomoea* plant named 'Emerald Splash' as illustrated and described.

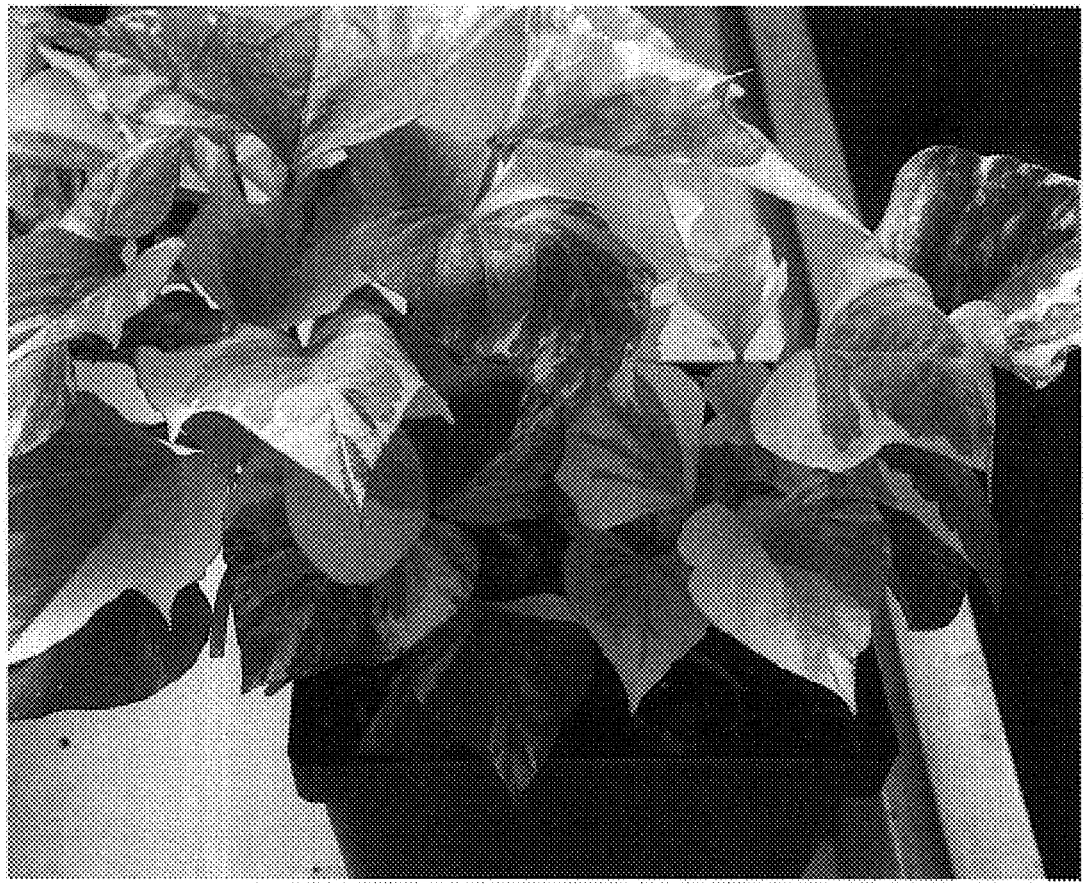

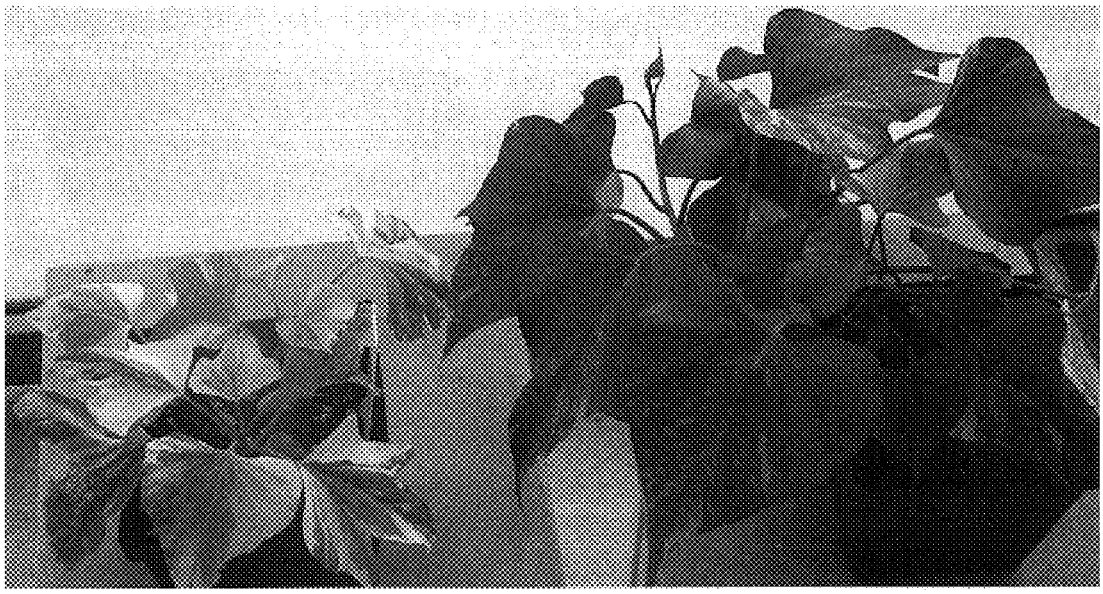

* * * * *